United States Patent
Huc et al.

(10) Patent No.: US 9,255,054 B2
(45) Date of Patent: Feb. 9, 2016

(54) HIGH-YIELD SYNTHESIS OF P-(BENZYLOXY)CALIX[6,7,8]ARENES

(71) Applicants: Vincent Germain Huc, Orsay (FR); Cyril Martini, Bures sur Yvette (FR)

(72) Inventors: Vincent Germain Huc, Orsay (FR); Cyril Martini, Bures sur Yvette (FR)

(73) Assignee: UNIVERSITE PARIS-SUD XI, Orsay Cedex (FR)

( * ) Notice: Subject to any disclaimer, the term of this patent is extended or adjusted under 35 U.S.C. 154(b) by 0 days.

(21) Appl. No.: 14/364,484

(22) PCT Filed: Dec. 11, 2012

(86) PCT No.: PCT/FR2012/052877
§ 371 (c)(1),
(2) Date: Jun. 11, 2014

(87) PCT Pub. No.: WO2013/088056
PCT Pub. Date: Jun. 20, 2013

(65) Prior Publication Data
US 2015/0011798 A1    Jan. 8, 2015

(30) Foreign Application Priority Data

Dec. 12, 2011 (FR) ..................... 11 61497
Aug. 28, 2012 (FR) ..................... 12 58051

(51) Int. Cl.
*C07C 41/30* (2006.01)
*C07C 43/23* (2006.01)

(52) U.S. Cl.
CPC ............. *C07C 41/30* (2013.01); *C07C 43/23* (2013.01); *C07C 2103/90* (2013.01)

(58) Field of Classification Search
None
See application file for complete search history.

(56) References Cited

U.S. PATENT DOCUMENTS 6,709,642 B1    3/2004    Dozol et al.

FOREIGN PATENT DOCUMENTS

FR    2797442 A1    2/2001

OTHER PUBLICATIONS

Casnati et al., "p-(Benzyloxy)calix[8]arene: One-Pot Synthesis and Functionalization", J. Org. Chem., 1997, vol. 62, No. 18. pp. 6236-6239.
Goodworth et al., "Synthesis and in vivo biological activity of large-ringed calixarenes against *Mycobacterium tuberculosis*", Tetrahedron, 2011, vol. 67, pp. 373-382.
Gutsche et al., "Calixarenes. 4. The Synthesis, Characterization, and Properties of the Calixarenes from p-tert-Butylphenol", J. Am. Chem. Soc., 1981, vol. 103, pp. 3782-3792, XP000676352.
Huc et al., "C3v (Trimethyl) p-(Benzyloxy)calix[6]arene: A Versatile Platform for the Synthesis of Functionalized C3v Calix[6]arenes", Eur. J. Org. Chem., 2010, pp. 2199-2205, XP55057188.
Huc et al., "p-(Benzyloxy)calix[8]arene Synthesis Revisited: p-(Benzyloxy)calix[4]-, p-(Benzyloxy)calix[5]-, p-(Benzyloxy)calix[7]-, and p-(Benzyloxy)bis(homooxa)calix[4]arenes", Eur. J. Org. Chem., 2010, pp. 6186-6192, XP55034558.
Markowitz et al., "Perforated Monolayers: Design and Synthesis of Porous and Cohesive Monolayers from Mercurated Calix[n]arenes", J. Am. Chem. Soc., 1989, vol. 111, pp. 8192-8200.
Nakayama et al., "A new positive-type photoresist based on mono-substituted hydroquinone calix[8]arene and diazonaphthoquinone", Journal of Materials Chemistry, 1999, vol. 9, pp. 697-702.
Ostaszewski et al., "Influence of Base and Solvent on the Reaction between p-Cresol and Formaldehyde Leading to p-Methylcalix[n]arenes", Polish J. Chem., 1997, vol. 71, pp. 1053-1059.
Vocanson et al., "Synthese du p-tert-butylcalix[7]arene. Optimisation du rendement par la methode des plans d'experiences", New J. Chem., 1995, vol. 19, pp. 825-829.
French Search Report, dated Apr. 11, 2013, from corresponding FR application.
International Search Report, dated Mar. 27, 2013, from corresponding PCT application.

*Primary Examiner* — Brian J Davis
(74) *Attorney, Agent, or Firm* — Young & Thompson

(57) ABSTRACT

The high-yield synthesis of p-(benzyloxy)calix[6,7,8]arenes by bringing caesium hydroxide into contact with p-(benzyloxy)phenol and paraformaldehyde, and composite materials including these p-(benzyloxy)calix[6,7,8]arenes.

14 Claims, No Drawings

HIGH-YIELD SYNTHESIS OF P-(BENZYLOXY)CALIX[6, 7,8]ARENES

The present invention relates to the high-yield synthesis of p-(benzyloxy)calix[6,7,8]arenes.

During the last ten years, calixarenes have been particularly studied because of the immense possibilities offered by these easily-accessible macrocycles. These macrocycles have the shape of a chalice, the cavity of which is less than or equal to approximately 1 nm.

Some of the most studied properties include ion and/or molecule recognition phenomena, supramolecular assemblies and the synthesis of nanoparticles.

In most cases, these studies have been carried out with calixarenes functionalized with a p-(t-butyl), given that the synthesis of these derivatives is by far the most documented since the pioneering work of Gutsche et al.

D. Gutsche, *Calixarenes: An Introduction*, The Royal Society of Chemistry, Cambridge, 2008.

(Z. Asfari, V. Böhmer, J. Harrowfield, J. Vicens (Eds.), *Calixarenes* 2001, Kluwer, Dordrecht, the Netherlands, 2001.

As a result, the use of other phenols functionalized for the synthesis of calixarenes is largely unexplored, even though one-stage syntheses of p-(alkyls)calixarenes are known (T. Patrick, P. Egan, *J. Org. Chem.* 1977, 42, 382; T. Patrick, P. Egan, *J. Org. Chem.* 1978, 43, 4280; Z. Asfari, J. Vicens, *Tetrahedron Lett.* 1988, 29, 2659; F. Vocanson, M. Perrin, R. Lamartine, *J. Inclusion Phenom. Macrocyclic Chem.* 2001, 39, 127; Jerry L. Atwood et al; *Org. Lett.* 1999, 1, 1523).

The p-substituted calixarenes are usually obtained in a mixture of calix[4, 5, 6, 7, 8] by reaction of a phenol p-substituted with paraformaldehyde in the presence of at least one base such as potash or soda (B. Dahwan et al. *Macromolec. Chem.* 1987, 188, 921; C. D. Gutsche et al. *Org. Synth.* 1990, 68, 234; C. D. Gutsche et al. *Org. Synth.* 1990, 68, 238).

Depending on the exact conditions used (nature of the alkaline base used as catalyst, temperature etc.) it is possible to direct the reaction in order to lead preferentially to a precise size of ring. In general, p-(t-Bu)calix[8]arene is the most easily-obtained calixarene, as it corresponds to the kinetic product of the polycondensation reaction.

p-(Benzyloxy)calix[6]arene is a calixarene already described in the literature in the neutralized form but obtained either as a very minority product of the synthesis of p-(benzyloxy)calix[8]arene, after several purification stages with a yield of 1 to 2% (A. Casnati et al., *J. Am. Chem. Soc.* 2001, 123, 12182-12190), or in a relatively impure form with a purity of the order of 80% (V. Huc et al., *Eur. J. Org. Chem.* 2010, 6186-6192).

p-(Benzyloxy)calix[7]arene comprises 7 repeat units in its structure. This size of ring is usually considered difficult to obtain in the field of calixarene chemistry. In fact, earlier studies show that calixarenes comprising an odd number of units are difficult to access and/or more difficult to purify. In the precise case of p-(benzyloxy)calix[7]arene, this product is already described as a very minority by-product of the synthesis of other calixarenes with yields of less than 10%, using complex purification procedures including column chromatography purifications (V. Huc et al., *Eur. J. Org. Chem.*, 2010, 6186-6192). Other calix[7]arenes are also known, in particular in the p-(t-Bu) series, but there too the yields are low (p-(t-Bu): A. Ninegawa et al., *Macromol. Chem. Rapid. Chem.* 1982, 3, 65; Y. Nakamoto et al. *Macromol. Chem. Rapid. Chem.* 1982, 3, 705; F. Vocanson et al., *New. J. Chem.* 1995, 19, 825; p-(benzyl): J. L. Atwood et al., *Org. Lett.* 1999, 1523).

p-(Benzyloxy)calix[7]arene in the monosalified form is not described in the literature and obtaining it would open up the way to novel functionalized calix[7]arenes, in particular based on salified phenol.

p-(Benzyloxy)calix[8]arene is obtained in the prior art with a yield of 48%, by reacting p-(benzyloxy)phenol in the presence of formaldehyde with a base selected from soda, potash or lithium hydroxide, the base being at a concentration of 0.02 equivalent with respect to the p-(benzyloxy)phenol (A Casnati et al. *J. Org. Chem.* 1997, 62, 6236-6239).

In most cases, the post-functionalization of the para position of these calixarenes (not always possible) is at best difficult. In the most common case of the p-(t-Bu) calixarenes, a process with several stages is generally involved, requiring the use of reagents to remove the tert-butyl. As the reaction is not quantitative, the deterbutylation becomes problematic when the number of calixarene units increases. The presence of by-products limits the yield, necessitates a purification stage and restricts the purity of the product. This can limit the final yield of completely deprotected product.

As a result, it remains an open question as to how to obtain calixarenes that can be easily functionalized on the high crown with a large variety of chemical groups under mild conditions and, in particular, how to obtain p-(benzyloxy)calix[6]arene and p-(benzyloxy)calix[7]arene that can be easily functionalized with yields of more than 50% and easy purification in a single stage.

One of the objects of the invention is to provide a synthesis process making it possible to:

obtain pure p-(benzyloxy)calix[6]arenes with a yield of more than 50% and a single-stage purification procedure by simple crystallization or, obtain p-(benzyloxy)calix[7]arene, with a yield of more than 50% and a single-stage purification procedure by simple selective filtration or crystallization from a mixture of organic solvents or, obtain p-(benzyloxy)calix[8]arene, with a yield of more than 50%, or obtain a mixture of the three, or of a mixture of two selected from the three.

Another object of the invention is to provide p-(benzyloxy)calix[7]arene in the form of a caesium monosalt.

Yet another object is the use of p-(benzyloxy)calix[6]arene or p-(benzyloxy)calix[7]arene or a mixture of the two, or a mixture of p-(benzyloxy)calix[6]arene or p-(benzyloxy)calix[7]arene for the constitution of a material.

The present invention relates to the use of at least one base, in particular selected from lithium hydroxide, potash, soda, rubidium hydroxide or caesium hydroxide, with p-(benzyloxy)phenol, said base being at a total concentration comprised from 0.09 to 0.5 equivalent with respect to said p-(benzyloxy)phenol, for the preparation of a mixture comprising p-(benzyloxy)calix[6]arene, p-(benzyloxy)calix[7]arene and p-(benzyloxy)calix[8]arene, or a mixture comprising p-(benzyloxy)calix[6]arene and p-(benzyloxy)calix[7]arene, or a mixture comprising p-(benzyloxy)calix[7]arene and p-(benzyloxy)calix[8]arene, or a mixture comprising p-(benzyloxy)calix[6]arene and p-(benzyloxy)calix[8]arene, or a compound consisting of p-(benzyloxy)calix[6]arene, p-(benzyloxy)calix[7]arene or p-(benzyloxy)calix[8]arene.

p-(Benzyloxy)calix[6]arene has the following structure:

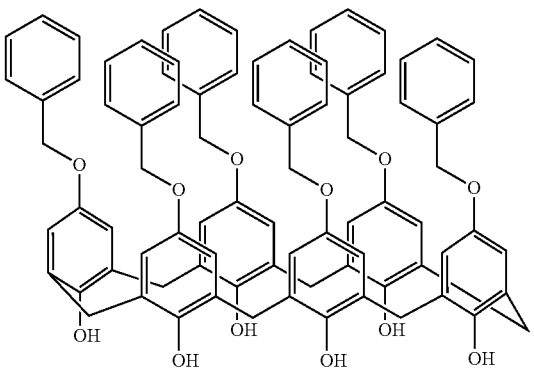 [SMILES: Oc1c2cc(OCc3ccccc3)cc1Cc1cc(OCc3ccccc3)cc(c1O)Cc1cc(OCc3ccccc3)cc(c1O)Cc1cc(OCc3ccccc3)cc(c1O)Cc1cc(OCc3ccccc3)cc(c1O)Cc1cc(OCc3ccccc3)cc(c1O)C2]

p-(Benzyloxy)calix[7]arene has the following structure:

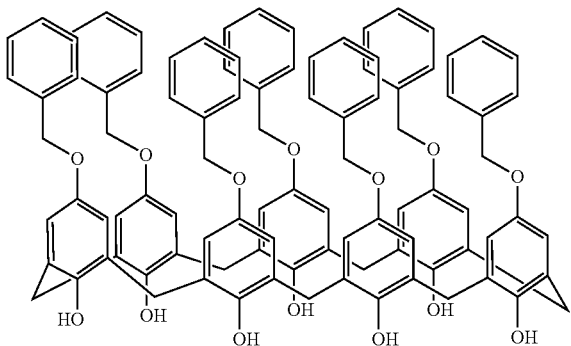 [SMILES: Oc1c2cc(OCc3ccccc3)cc1Cc1cc(OCc3ccccc3)cc(c1O)Cc1cc(OCc3ccccc3)cc(c1O)Cc1cc(OCc3ccccc3)cc(c1O)Cc1cc(OCc3ccccc3)cc(c1O)Cc1cc(OCc3ccccc3)cc(c1O)Cc1cc(OCc3ccccc3)cc(c1O)C2]

p-(Benzyloxy)calix[8]arene has the following structure:

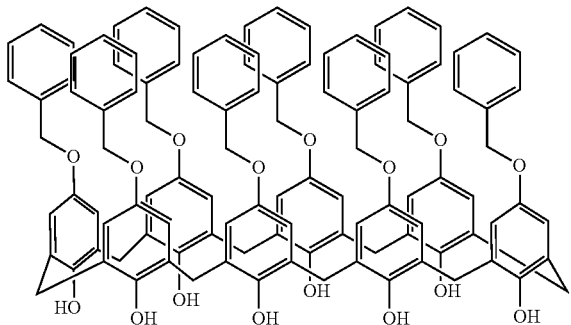 [SMILES: Oc1c2cc(OCc3ccccc3)cc1Cc1cc(OCc3ccccc3)cc(c1O)Cc1cc(OCc3ccccc3)cc(c1O)Cc1cc(OCc3ccccc3)cc(c1O)Cc1cc(OCc3ccccc3)cc(c1O)Cc1cc(OCc3ccccc3)cc(c1O)Cc1cc(OCc3ccccc3)cc(c1O)Cc1cc(OCc3ccccc3)cc(c1O)C2]

The present invention relates to the use of at least one base, in particular caesium hydroxide, with p-(benzyloxy)phenol, said base being at a total concentration comprised from 0.09 to 0.5 equivalent with respect to said p-(benzyloxy)phenol, for the preparation of a mixture comprising p-(benzyloxy)calix[6]arene and p-(benzyloxy)calix[7]arene, or a compound consisting of p-(benzyloxy)calix[6]arene or p-(benzyloxy)calix[7]arene.

The Inventors have surprisingly found that the combination of at least one base such as caesium hydroxide and a total concentration comprised from 0.09 to 0.5 equivalent with respect to said p-(benzyloxy)phenol made it possible to obtain p-(benzyloxy)calix[6]arene and p-(benzyloxy)calix[7]arene at more than 50%.

In an advantageous embodiment, said mixture comprising p-(benzyloxy)calix[6]arene and p-(benzyloxy)calix[7]arene, obtained with caesium hydroxide at a total concentration comprised from 0.09 to 0.5 equivalent and p-(benzyloxy)phenol, is in the majority, i.e. is obtained in a proportion of more than 50% (determined by NMR), and a mixture of p-(benzyloxy)calix[9-20]arenes in a minority proportion is also obtained.

By mixture of p-(benzyloxy)calix[9-20]arenes, is meant a mixture of p-(benzyloxy)calix[9]arene, p-(benzyloxy)calix[10]arene, p-(benzyloxy)calix[11]arene, p-(benzyloxy)calix[12]arene, p-(benzyloxy)calix[13]arene, p-(benzyloxy)calix[14]arene, p-(benzyloxy)calix[15]arene, p-(benzyloxy)calix[16]arene, p-(benzyloxy)calix[17]arene, p-(benzyloxy)calix[18]arene, p-(benzyloxy)calix[19]arene, p-(benzyloxy)calix[9-20]arene, each of them being able to be present in a proportion of 0 to 100% by weight, provided that at least one of them is present in a proportion different from 0% and provided that the sum of the percentage of each of them is equal to 100%, in said mixture of p-(benzyloxy)calix[9-20]arenes.

The p-(benzyloxy)calix[9-20]arenes are also referred to as large calixarenes in the description.

The present invention relates to the use of at least one base, in particular rubidium hydroxide, with p-(benzyloxy)phenol, said base being at a total concentration comprised from 0.09 to 0.5 equivalent with respect to said p-(benzyloxy)phenol, for the preparation of a mixture comprising p-(benzyloxy)calix[6]arene, p-(benzyloxy)calix[7]arene and p-(benzyloxy)calix[8]arene and a mixture of p-(benzyloxy)calix[9-20]arenes.

The present invention relates to the use of at least one base, in particular rubidium hydroxide, with p-(benzyloxy)phenol, said base being at a total concentration comprised from 0.09 to 0.3 equivalent with respect to said p-(benzyloxy)phenol, for the preparation of a mixture comprising p-(benzyloxy)calix[6]arene, p-(benzyloxy)calix[7]arene and p-(benzyloxy)calix[8]arene and a mixture of p-(benzyloxy)calix[9-20]arenes.

The Inventors have surprisingly found that the combination of at least one base such as rubidium hydroxide and a total concentration comprised from 0.09 to 0.3 equivalent with respect to said p-(benzyloxy)phenol made it possible to obtain a mixture of p-(benzyloxy)calix[6]arene and p-(benzyloxy)calix[7]arene at 50% or more, as well as the mixture of p-(benzyloxy)calix[9-20]arenes.

The present invention relates to the use of at least one base, in particular selected from potash and soda, with p-(benzyloxy)phenol, said at least one base being at a total concentration comprised from 0.09 to 0.5 equivalent with respect to said p-(benzyloxy)phenol, for the preparation of a mixture comprising p-(benzyloxy)calix[6]arene, p-(benzyloxy)calix[7]arene and p-(benzyloxy)calix[8]arene, or a mixture comprising p-(benzyloxy)calix[7]arene and p-(benzyloxy)calix[8]arene, or a mixture comprising p-(benzyloxy)calix[6]arene and p-(benzyloxy)calix[8]arene, or a mixture comprising p-(benzyloxy)calix[6]arene and p-(benzyloxy)calix[7]arene, or a compound consisting of p-(benzyloxy)calix[6]arene, p-(benzyloxy)calix[7]arene or p-(benzyloxy)calix[8]arene.

The inventors have surprisingly found that the combination of at least one base such as potash and/or soda and a total concentration comprised from 0.09 to 0.5 equivalent with respect to said p-(benzyloxy)phenol made it possible to obtain p-(benzyloxy)calix[6]arene or p-(benzyloxy)calix[7]arene or p-(benzyloxy)calix[8]arene as a majority product, or a mixture thereof or a mixture of two among the three, depending on the total concentration of base introduced, with good yields.

The use of KOH or NaOH at a concentration less than 0.09 equivalent (e.g. 0.03 equivalent) essentially leads to p-(benzyloxy)calix[8]arene.

One of the advantages of the invention is therefore the provision of p-(benzyloxy)calix[6]arene or p-(benzyloxy)calix[7]arene or p-(benzyloxy)calix[8]arene or a mixture thereof, the benzyloxy functions of which are deprotected under very mild conditions, by simple debenzylation using techniques well known to a person skilled in the art, thus allowing access to molecules which can be easily functionalized subsequently.

According to another aspect, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene, comprising a stage of bringing caesium hydroxide into contact with p-(benzyloxy)phenol and paraformaldehyde, said one base being at a total concentration comprised from 0.09 to 0.5 equivalent with respect to said p-(benzyloxy)phenol.

According to another aspect, the present invention relates to a process for the preparation of a compound consisting of a mixture comprising p-(benzyloxy)calix[9-20]arenes, p-(benzyloxy)calix[6]arene, p-(benzyloxy)calix[7]arene, and p-(benzyloxy)calix[8]arene comprising a stage of bringing rubidium hydroxide into contact with p-(benzyloxy)phenol and paraformaldehyde, said one base being at a total concentration comprised from 0.09 to 0.5 equivalent with respect to said p-(benzyloxy)phenol.

According to another aspect, the present invention relates to a process for the preparation of a compound consisting of a mixture comprising p-(benzyloxy)calix[9-20]arenes, p-(benzyloxy)calix[6]arene, p-(benzyloxy)calix[7]arene, and p-(benzyloxy)calix[8]arene comprising a stage of bringing rubidium hydroxide into contact with p-(benzyloxy)phenol and paraformaldehyde, said one base being at a total concentration comprised from 0.09 to 0.3 equivalent with respect to said p-(benzyloxy)phenol.

According to another aspect the present invention relates to a process for the preparation of a compound consisting of a mixture comprising p-(benzyloxy)calix[6]arene, p-(benzyloxy)calix[7]arene and p-(benzyloxy)calix[8]arene, or a compound consisting of p-(benzyloxy)calix[6]arene, p-(benzyloxy)calix[7]arene or p-(benzyloxy)calix[8]arene, comprising bringing at least one base selected from soda or potash into contact with p-(benzyloxy)phenol and paraformaldehyde, said base being at a total concentration comprised from 0.09 to 0.5 equivalent with respect to said p-(benzyloxy)phenol.

According to another aspect the present invention relates to a process for the preparation of a compound consisting of a mixture comprising p-(benzyloxy)calix[6]arene, p-(benzyloxy)calix[7]arene and p-(benzyloxy)calix[8]arene, or a mixture comprising p-(benzyloxy)calix[6]arene and p-(benzyloxy)calix[8]arene, or a compound consisting of p-(benzyloxy)calix[6]arene, p-(benzyloxy)calix[7]arene or p-(benzyloxy)calix[8]arene, comprising bringing at least one base selected from soda or potash into contact with p-(benzyloxy)phenol and paraformaldehyde, said base being at a total concentration comprised from 0.09 to 0.2 equivalent, in particular 0.15 equivalent, with respect to said p-(benzyloxy)phenol.

In an advantageous embodiment, the present invention relates to a process for the preparation of a compound consisting of a mixture comprising p-(benzyloxy)calix[6]arene, p-(benzyloxy)calix[7]arene and p-(benzyloxy)calix[8]arene, or a mixture comprising p-(benzyloxy)calix[6]arene and p-(benzyloxy)calix[8]arene, or a compound consisting of p-(benzyloxy)calix[7]arene, comprising bringing at least one base selected from soda or potash into contact with p-(benzyloxy)phenol and paraformaldehyde, said base being at a total concentration comprised from 0.09 to 0.2 equivalent, in particular 0.15 equivalent, with respect to said p-(benzyloxy)phenol, as defined above, in order to obtain a mixture of p-(benzyloxy)calix[6]arene, p-(benzyloxy)calix[7]arene and p-(benzyloxy)calix[8]arene, comprising an additional stage of filtration of the mixture comprising p-(benzyloxy)calix[6]arene, p-(benzyloxy)calix[7]arene and p-(benzyloxy)calix[8]arene in order to obtain, on the one hand, a precipitate comprising a compound consisting of p-(benzyloxy)calix[7]arene in the neutralized form and, on the other hand, a filtrate comprising a mixture of different compounds comprising p-(benzyloxy)calix[6]arene.

By the expression "in the neutralized form", is meant a calixarene all the free phenol groups of which have been neutralized, i.e. are in the OH, non-salified form.

An advantage of the invention is therefore being able to easily obtain p-(benzyloxy)calix[7]arene in the neutralized form by simple filtration of the reaction medium.

The inventors have surprisingly found that the combination of at least one base such as soda or potash at a total concentration comprised from 0.09 to 0.2 equivalent, with respect to said p-(benzyloxy)phenol made it possible to obtain a mixture comprising p-(benzyloxy)calix[6]arene, p-(benzyloxy)calix[7]arene and p-(benzyloxy)calix[8]arene, from which the p-(benzyloxy)calix[7]arene in the neutralized form can be separated and obtained pure by simple filtration.

Throughout the description, the term "pure" denotes a compound having a purity greater than 95%.

According to another aspect the present invention relates to a process for the preparation of a compound consisting of a mixture comprising p-(benzyloxy)calix[6]arene, p-(benzyloxy)calix[7]arene and p-(benzyloxy)calix[8]arene, or a mixture comprising p-(benzyloxy)calix[6]arene and p-(benzyloxy)calix[8]arene, or a compound consisting of p-(benzyloxy)calix[6]arene, p-(benzyloxy)calix[7]arene or p-(benzyloxy)calix[8]arene, comprising bringing at least one base selected from soda or potash into contact with p-(benzyloxy)phenol and paraformaldehyde, said base being at a total concentration greater than 0.2 equivalent and less than or equal to 0.5 equivalent, in particular 0.3 equivalent, with respect to said p-(benzyloxy)phenol.

In an advantageous embodiment, the present invention relates to a process for the preparation of a compound consisting of a mixture comprising p-(benzyloxy)calix[6]arene, and p-(benzyloxy)calix[7]arene, or a compound consisting of p-(benzyloxy)calix[8]arene, comprising bringing at least one base selected from soda or potash into contact with p-(benzyloxy)phenol and paraformaldehyde, said base being at a total concentration greater than 0.2 equivalent and less than or equal to 0.5 equivalent, in particular 0.3 equivalent, with respect to said p-(benzyloxy)phenol as defined above, in order to obtain a mixture of p-(benzyloxy)calix[6]arene, p-(benzyloxy)calix[7]arene and p-(benzyloxy)calix[8]arene, comprising an additional stage of filtration of the mixture comprising p-(benzyloxy)calix[6]arene, p-(benzyloxy)calix[7]arene and p-(benzyloxy)calix[8]arene in order to obtain, on the one hand, a precipitate comprising a compound consisting of pure p-(benzyloxy)calix[8]arene in the neutralized form and, on the other hand, a filtrate comprising a mixture comprising p-(benzyloxy)calix[6]arene and p-(benzyloxy) calix[7]arene in the neutralized form.

By the expression "in the neutralized form", is meant a calixarene, all the phenol groups of which have been neutralized, i.e. are in the OH, non-salified form.

An advantage of the invention is therefore being able to easily obtain p-(benzyloxy)calix[8]arene in the neutralized form by simple filtration of the reaction medium.

The filtrate makes it possible to recover the mixture of p-(benzyloxy)calix[6]arene and p-(benzyloxy)calix[7]arene in the neutralized form.

The inventors have surprisingly found that the combination of at least one base such as soda or potash at a total concentration greater than 0.2 equivalent and less than or equal to 0.5 equivalent with respect to said p-(benzyloxy)phenol made it possible to obtain a mixture comprising p-(benzyloxy)calix [6]arene, p-(benzyloxy)calix[7]arene and p-(benzyloxy) calix[8]arene, from which the p-(benzyloxy)calix[8]arene in the neutralized form can be separated and obtained pure by simple filtration.

In an advantageous embodiment, the present invention relates to a process for the preparation of a compound consisting of p-(benzyloxy)calix[6]arene, or p-(benzyloxy)calix [7]arene, comprising bringing at least one base selected from soda or potash into contact with p-(benzyloxy)phenol and paraformaldehyde, said base being at a total concentration greater than 0.2 equivalent and less than or equal to 0.5 equivalent, in particular 0.3 equivalent, with respect to said p-(benzyloxy)phenol and an additional stage of filtration of the mixture comprising p-(benzyloxy)calix[6]arene, p-(benzyloxy)calix[7]arene and p-(benzyloxy)calix[8]arene in order to obtain, on the one hand, a precipitate comprising p-(benzyloxy)calix[8]arene in the neutralized form and, on the other hand, a filtrate comprising a mixture comprising p-(benzyloxy)calix[6]arene and p-(benzyloxy)calix[7]arene in the neutralized form, as defined above and, comprising an additional stage of treatment of the filtrate containing the mixture comprising p-(benzyloxy)calix[6] arene and p-(benzyloxy)calix[7]arene with a mixture of solvents comprising DMSO, in order to obtain, on the one hand, a precipitate consisting of p-(benzyloxy)calix[6]arene and, on the other hand, a filtrate containing p-(benzyloxy)calix[7] arene in the neutralized form.

The inventors have surprisingly found that the treatment of the above filtrate, obtained after filtration of the p-(benzyloxy)calix[8]arene, with a mixture of solvent comprising DMSO, made it possible to separate the p-(benzyloxy)calix [6]arene from the p-(benzyloxy)calix[7]arene and thus obtain in particular pure p-(benzyloxy)calix[7]arene with a yield greater than 50%.

The DMSO is mixed with a non-polar solvent, such as toluene, in a proportion of 1 to 10 by volume.

By "non-polar solvent", is meant a solvent possessing a weak or zero dipole moment, such as, without being limited to, benzene, toluene, xylene, cyclohexane, hexane, pentane, petroleum ether, carbon tetrachloride etc.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene comprising a stage of bringing caesium hydroxide into contact with p-(benzyloxy)phenol and paraformaldehyde, in which said base is at a total concentration comprised from 0.09 to 0.5 equivalent in order to obtain a mixture comprising p-(benzyloxy)calix[6]arene and p-(benzyloxy)calix[7]arene, and comprising an additional stage of neutralization in order to obtain a mixture comprising p-(benzyloxy)calix[6]arene and p-(benzyloxy)calix[7]arene in the neutralized form.

The calixarenes obtained in the reaction medium are in a basic environment and therefore require a stage of neutralization, i.e. treatment with an acid in order to obtain them in the neutralized form.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene, comprising a stage of bringing caesium hydroxide into contact with p-(benzyloxy)phenol and paraformaldehyde, in which said base is at a total concentration comprised from 0.09 to 0.2 equivalent, in particular 0.15 equivalent, in order to obtain a mixture comprising p-(benzyloxy)calix[6]arene and p-(benzyloxy)calix[7]arene in the salified form.

The inventors have surprisingly found that controlling the quantity of base such as caesium hydroxide, i.e. comprised from 0.09 to 0.2 equivalent with respect to the p-(benzyloxy) phenol, made it possible to control the reaction and promote the formation of p-(benzyloxy)calix[7]arene with respect to p-(benzyloxy)calix[6]arene, thus leading to a mixture comprising a majority of p-(benzyloxy)calix[7]arene.

Advantageously, the concentration of caesium is 0.10 equivalent or 0.11 equivalent or 0.12 equivalent or 0.13 equivalent or 0.14 equivalent or 0.15 equivalent or 0.16 equivalent or 0.17 equivalent or 0.18 equivalent or 0.19 equivalent or 0.20 equivalent.

More advantageously, the concentration of caesium is 0.15 equivalent.

In an advantageous embodiment, the mixture comprising p-(benzyloxy)calix[6]arene and p-(benzyloxy)calix[7]arene obtained by the process in which the caesium hydroxide is at a total concentration comprised from 0.09 to 0.2 equivalent, in particular 0.15 equivalent, comprises from 50 to 80% by weight of p-(benzyloxy)calix[7]arene, in particular 70%, and of 20 to 50% by weight of p-(benzyloxy)calix[6]arene.

The percentages indicated here are determined by NMR.

In an advantageous embodiment, the present invention relates to a process for the preparation of a compound consisting of a mixture comprising p-(benzyloxy)calix[6]arene and p-(benzyloxy)calix[7]arene, a compound consisting of p-(benzyloxy)calix[6]arene or p-(benzyloxy)calix[7]arene, comprising a stage of bringing at least one base selected from caesium hydroxide into contact with p-(benzyloxy)phenol and paraformaldehyde, in which said base is at a total concentration comprised from 0.09 to 0.2 equivalent, in particular 0.15 equivalent, in order to obtain a mixture comprising p-(benzyloxy)calix[6]arene and p-(benzyloxy)calix[7]arene in the salified form, and comprising an additional stage of filtration of the mixture comprising p-(benzyloxy)calix[6] arene and p-(benzyloxy)calix[7]arene in the salified form in order to obtain p-(benzyloxy)calix[7]arene in the form of a caesium monosalt followed by an additional stage of neutralization of p-(benzyloxy)calix[7]arene in the form of a caesium monosalt in order to obtain p-(benzyloxy)calix[7]arene in the neutralized form.

Even more unexpectedly, the inventors have found that p-(benzyloxy)calix[7]arene which is in the salified form, i.e. a phenol present on the molecule is in the form of caesium phenolate, can be isolated mostly in the form of a caesium monosalt.

It must be noted that obtaining an isolated caesium monosalt is all the more unexpected as the process involving soda or potash at 0.15 equivalent as base, after filtration, does not lead to the precipitation of p-(benzyloxy)calix[7]arene in the salified form.

This can be explained by the fact that caesium is a so-called soft alkaline, caesium phenolate can be stabilized by interactions with the pi-conjugated systems of the phenyl functions present on the calixarene thus making it possible to isolate the most thermodynamically stable product. Such interactions are much weaker with the lower alkalines.

Another explanation could be a lower solubility of the caesium monosalt with respect to the other alkaline salts. This low solubility could induce precipitation of this monosalt out of the reaction medium as it is formed, and thus shift the different equilibriums.

Another advantage of the invention is that the provision of p-(benzyloxy)calix[7]arene in the form of a caesium salt allows the functionalization of the caesium phenolate function by an electrophilic compound before the deprotection of the benzyloxy groups, thus allowing access to functionalized molecules different from those obtained above.

Apart from obtaining the caesium monosalt, the process developed by the Inventors makes it possible to substantially increase the reaction's yield of p-(benzyloxy)calix[7]arene which is greater than or equal to 50%, unlike that of the prior art which does not exceed 10%.

In an advantageous embodiment, the present invention relates to a process for the preparation of a compound consisting of a mixture comprising p-(benzyloxy)calix[6]arene and p-(benzyloxy)calix[7]arene defined above, comprising the following stages:
   a. bringing caesium hydroxide at a concentration of 0.09 to 0.2 equivalent, in particular 0.15 equivalent, into contact with p-(benzyloxy)phenol and paraformaldehyde in a solvent, then heating in order to obtain a mixture comprising p-(benzyloxy)calix[6]arene and p-(benzyloxy)calix[7]arene in the salified form,
   b. neutralization of the mixture comprising p-(benzyloxy)calix[6]arene and p-(benzyloxy)calix[7]arene in the salified form with an acid, in order to obtain a mixture comprising p-(benzyloxy)calix[6]arene and p-(benzyloxy)calix[7]arene in the neutralized form.

The solvent of stage a. is a solvent with a high boiling point comprised between approximately 100 and approximately 200° C., in particular approximately 140° C., for example xylene, but without being limited thereto.

The heating therefore depends on the nature of the solvent and can be carried out from 30° C. to 200° C.

Stage a. leads to a mixture of p-(benzyloxy)calix[6]arene and p-(benzyloxy)calix[7]arene in the salified form.

The neutralization of the mixture is carried out with an acid, for example aqueous hydrochloric acid or aqueous sulphuric acid.

In this embodiment, a mixture of p-(benzyloxy)calix[6]arene and p-(benzyloxy)calix[7]arene in the neutralized form is therefore obtained.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene, comprising the following stages:
   a. bringing caesium hydroxide at a concentration of 0.09 to 0.2 equivalent, in particular 0.15 equivalent, into contact with p-(benzyloxy)phenol and paraformaldehyde in a solvent, then heating, in order to obtain a mixture comprising p-(benzyloxy)calix[6]arene and p-(benzyloxy)calix[7]arene in the salified form,
   b. filtration of said mixture comprising p-(benzyloxy)calix[6]arene and p-(benzyloxy)calix[7]arene in the salified form in order to obtain p-(benzyloxy)calix[7]arene in the form of a caesium monosalt,
   c. optionally neutralization of the p-(benzyloxy)calix[7]arene in the form of a caesium monosalt with an acid in order to obtain p-(benzyloxy)calix[7]arene in the neutralized form.

Stage a. leads to a mixture of p-(benzyloxy)calix[6]arene and p-(benzyloxy)calix[7]arene in the salified form but only p-(benzyloxy)calix[7]arene in the form of a caesium salt precipitates, which makes it possible to isolate it pure by simple filtration in stage b.

The p-(benzyloxy)calix[7]arene can then be used as it is for functionalization of the caesium phenolate function, or manufacture of a material, or then neutralized for a functionalization of the phenol functions released after debenzylation.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene, comprising a stage bringing caesium hydroxide at a concentration of 0.09 to 0.2 equivalent, in particular 0.15 equivalent into contact, in order to obtain a mixture comprising p-(benzyloxy)calix[6]arene and p-(benzyloxy)calix[7]arene in the salified form, as defined above, in which the solvent, in particular xylene, is heated under reflux.

In an advantageous embodiment, the present invention relates to a process for the preparation of a compound consisting of a mixture comprising p-(benzyloxy)calix[6]arene, p-(benzyloxy)calix[7]arene, or a compound consisting of p-(benzyloxy)calix[6]arene or p-(benzyloxy)calix[7]arene, comprising a stage of bringing caesium hydroxide into contact with p-(benzyloxy)phenol and paraformaldehyde, in which said base is at a total concentration greater than 0.2 equivalent and less than or equal to 0.5 equivalent, in particular 0.3 equivalent, in order to obtain a mixture comprising p-(benzyloxy)calix[6]arene and p-(benzyloxy)calix[7]arene in the salified form.

Completely unexpectedly, the Inventors have found that the use of caesium hydroxide at a total concentration greater than 0.2 equivalent and less than or equal to 0.5 equivalent made it possible to obtain a mixture comprising p-(benzyloxy)calix[6]arene and p-(benzyloxy)calix[7]arene in the salified form in which the p-(benzyloxy)calix[6]arene is in the majority and the p-(benzyloxy)calix[7]arene in the salified form does not precipitate, unlike the process defined above in which caesium hydroxide is used at a total concentration comprised from 0.09 to 0.2 equivalent.

In an advantageous embodiment, the total concentration of caesium hydroxide is 0.21 equivalent, or 0.22 equivalent, or 0.23 equivalent, or 0.24 equivalent, or 0.25 equivalent, or 0.26 equivalent, or 0.27 equivalent, or 0.28 equivalent, or 0.29 equivalent.

In an advantageous embodiment, the mixture comprising p-(benzyloxy)calix[6]arene and p-(benzyloxy)calix[7]arene obtained by the process in which caesium hydroxide is at a total concentration greater than 0.2 equivalent and less than or equal to 0.5 equivalent, in particular 0.3 equivalent, comprises from 50 to 80% by weight of p-(benzyloxy)calix[6]arene and 10 to 20% by weight of p-(benzyloxy)calix[7]arene.

The percentages indicated here are determined by NMR.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene comprising a stage of bringing caesium hydroxide into contact with p-(benzyloxy)phenol and paraformaldehyde, in which said base is at a total concentration greater than 0.2 equivalent and less than or equal to 0.5 equivalent, in particular 0.3 equivalent, in order to obtain a mixture comprising p-(benzyloxy)calix[6]arene and p-(benzyloxy)calix[7]arene in the salified form, as defined above, comprising an additional stage of neutralization of the mixture comprising p-(benzyloxy)calix[6]arene and p-(benzyloxy)calix[7]arene obtained in the salified form in order to obtain a mixture comprising p-(benzyloxy)calix[6]arene and p-(benzyloxy)calix[7]arene in the neutralized form.

In an advantageous embodiment, the present invention relates to a process for the preparation of a compound consisting of a mixture comprising p-(benzyloxy)calix[6]arene, p-(benzyloxy)calix[7]arene, or a compound consisting of p-(benzyloxy)calix[6]arene or p-(benzyloxy)calix[7]arene comprising a stage of bringing caesium hydroxide into contact with p-(benzyloxy)phenol and paraformaldehyde, in which said base is at a total concentration greater than 0.2 equivalent and less than or equal to 0.5 equivalent, in particular 0.3 equivalent, in order to obtain a mixture comprising p-(benzyloxy)calix[6]arene and p-(benzyloxy)calix[7]arene in the salified form, comprising an additional stage of neutralization of the mixture comprising p-(benzyloxy)calix[6]arene and p-(benzyloxy)calix[7]arene obtained in the salified form in order to obtain a mixture comprising p-(benzyloxy)calix[6]arene and p-(benzyloxy)calix[7]arene in the neutralized form, as defined above, comprising an additional stage of crystallization of the mixture comprising p-(benzyloxy)calix[6]arene and p-(benzyloxy)calix[7]arene in the neutralized form from a mixture of DMSO- or DMF-based solvents in order to obtain p-(benzyloxy)calix[6]arene in the neutralized form.

The Inventors have also found that the treatment of the mixture comprising p-(benzyloxy)calix[6]arene and p-(benzyloxy)calix[7]arene in the neutralized form in a mixture of DMSO- or DMF-based solvents made it possible to isolate pure p-(benzyloxy)calix[6]arene with an excellent yield, greater than 50%, and very high purity (95%), unlike the prior art.

By the expression "DMSO- or DMF-based solvent", is meant a mixture of solvents comprising at least 10% by volume of DMSO or DMF.

The DMSO or DMF make it possible to solubilize the colloid formed by the mixture comprising p-(benzyloxy)calix[6]arene and p-(benzyloxy)calix[7]arene in the neutralized form.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene as defined above, comprising the following stages:
  a. bringing caesium hydroxide at a total concentration greater than 0.2 equivalent and less than or equal to 0.5 equivalent, in particular 0.3 equivalent, into contact with p-(benzyloxy)phenol and formaldehyde in a solvent, then heating in order to obtain a mixture comprising p-(benzyloxy)calix[6]arene and p-(benzyloxy)calix[7]arene in the salified form,
  b. neutralization of said mixture comprising p-(benzyloxy)calix[6]arene and p-(benzyloxy)calix[7]arene in the salified form with an acid in order to obtain a mixture comprising p-(benzyloxy)calix[6]arene and p-(benzyloxy)calix[7]arene in the neutralized form,
  c. optionally, crystallization of the mixture comprising p-(benzyloxy)calix[6]arene and p-(benzyloxy)calix[7]arene in the neutralized form from a mixture of DMSO- or DMF-based solvents in order to obtain p-(benzyloxy)calix[6]arene in the neutralized form.

The solvent of stage a. is a solvent with a high boiling point comprised between approximately 100 and approximately 200° C., in particular approximately 140° C., for example xylene, but without being limited thereto.

The heating therefore depends on the nature of the solvent and can be carried out from 30° C. to 200° C.

Stage a. leads to a mixture of p-(benzyloxy)calix[6]arene and p-(benzyloxy)calix[7]arene in the salified form.

The neutralization of the mixture is carried out with an acid, for example aqueous hydrochloric acid or aqueous sulphuric acid.

After crystallization from a mixture of DMSO- or DMF-based solvents when it takes place, the mixture comprising p-(benzyloxy)calix[6]arene and p-(benzyloxy)calix[7]arene in the neutralized form is filtered in order to obtain p-(benzyloxy)calix[6]arene in the neutralized form (precipitate) and p-(benzyloxy)calix[7]arene (filtrate) separately.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene, as defined above, comprising the following stages:
  a. bringing caesium hydroxide at a total concentration greater than 0.2 equivalent and less than or equal to 0.5 equivalent, in particular 0.3 equivalent, into contact with p-(benzyloxy)phenol and formaldehyde in a solvent, then heating in order to obtain a mixture comprising p-(benzyloxy)calix[6]arene and p-(benzyloxy)calix[7]arene in the salified form,
  b. neutralization of said mixture comprising p-(benzyloxy)calix[6]arene and p-(benzyloxy)calix[7]arene in the salified form with an acid in order to obtain a mixture comprising p-(benzyloxy)calix[6]arene and p-(benzyloxy)calix[7]arene in the neutralized form,
  c. crystallization of said mixture comprising p-(benzyloxy)calix[6]arene and p-(benzyloxy)calix[7]arene in the neutralized form from a mixture of DMSO-based solvents in order to obtain p-(benzyloxy)calix[6]arene in the neutralized form.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene, comprising bringing caesium hydroxide at a total concentration greater than 0.2 equivalent and less than or equal to 0.5 equivalent, in particular 0.3 equivalent, into contact with p-(benzyloxy)phenol and formaldehyde, as defined above, in which the solvent, in particular xylene, is heated under reflux.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene comprising bringing caesium hydroxide at a total concentration greater than 0.2 equivalent and less than or equal to 0.5 equivalent, in particular 0.3 equivalent, into contact with p-(benzyloxy)phenol and formaldehyde, as defined above, in which the mixture of solvents of the crystallization stage comprises DMSO and a moderately polar solvent such as acetone.

By "moderately polar solvent", is meant a solvent possessing a dipole moment close to that of acetone.

The DMSO or DMF is mixed with a moderately polar solvent such as acetone in a proportion of 10% to 90% by volume.

The crystallization filtrate then contains p-(benzyloxy) calix[7]arene in the neutralized form.

According to another aspect, the present invention relates to a process for the preparation of a compound consisting of a mixture comprising p-(benzyloxy)calix[9-20]arenes, p-(benzyloxy)calix[6]arene, p-(benzyloxy)calix[7]arene and p-(benzyloxy)calix[8]arene, comprising a stage of bringing rubidium hydroxide into contact with p-(benzyloxy)phenol and paraformaldehyde, in which said base is at a total concentration greater than 0.2 equivalent and less than or equal to 0.5 equivalent, in particular less than or equal to 0.3 equivalent, in order to obtain a mixture comprising p-(benzyloxy) calix[9-20]arenes, p-(benzyloxy)calix[6]arene, p-(benzyloxy)calix[7]arene and p-(benzyloxy)calix[8]arene in the salified form.

Completely unexpectedly, the Inventors have found that the use of rubidium hydroxide at a total concentration greater than 0.2 equivalent and less than or equal to 0.3 equivalent made it possible to obtain a mixture comprising approximately 50% by weight of a mixture of p-(benzyloxy)calix[6] arene, p-(benzyloxy)calix[7]arene and p-(benzyloxy)calix [8]arene in the salified form, as well as a mixture of p-(benzyloxy)calix[9-20]arenes in the salified form, at approximately 50% by weight.

In an advantageous embodiment, the total concentration of rubidium hydroxide is 0.21 equivalent, or 0.22 equivalent, or 0.23 equivalent, or 0.24 equivalent, or 0.25 equivalent, or 0.26 equivalent, or 0.27 equivalent, or 0.28 equivalent, or 0.29 equivalent.

In an advantageous embodiment, the present invention relates to a process for the preparation of a compound consisting of a mixture comprising p-(benzyloxy)calix[9-20]arenes, p-(benzyloxy)calix[6]arene, p-(benzyloxy)calix[7] arene and p-(benzyloxy)calix[8]arene, comprising a stage of bringing rubidium hydroxide into contact with p-(benzyloxy) phenol and paraformaldehyde, in which said base is at a total concentration greater than 0.2 equivalent and less than or equal to 0.5 equivalent, in particular less than or equal to 0.3 equivalent, in order to obtain a mixture comprising p-(benzyloxy)calix[9-20]arenes, p-(benzyloxy)calix[6]arene, p-(benzyloxy)calix[7]arene and p-(benzyloxy)calix[8]arene, in the salified form, as defined above, comprising an additional stage of neutralization of the mixture comprising p-(benzyloxy)calix[9-20]arenes, p-(benzyloxy)calix[6] arene, p-(benzyloxy)calix[7]arene and p-(benzyloxy)calix [8]arene, in the neutralized form.

In an advantageous embodiment, the present invention relates to a process for the preparation of a compound consisting of a mixture comprising p-(benzyloxy)calix[9-20]arenes, p-(benzyloxy)calix[6]arene, p-(benzyloxy)calix[7] arene and p-(benzyloxy)calix[8]arene, comprising a stage of bringing rubidium hydroxide into contact with p-(benzyloxy) phenol and paraformaldehyde, in which said base is at a total concentration greater than 0.2 equivalent and less than or equal to 0.5 equivalent, in particular less than or equal to 0.3 equivalent, in order to obtain a mixture comprising p-(benzyloxy)calix[9-20]arenes, p-(benzyloxy)calix[6]arene, p-(benzyloxy)calix[7]arene and p-(benzyloxy)calix[8]arene, in the salified form, comprising an additional stage of neutralization of the mixture comprising p-(benzyloxy)calix[9-20]arenes, p-(benzyloxy)calix[6]arene, p-(benzyloxy)calix [7]arene and p-(benzyloxy)calix[8]arene obtained in the salified form in order to obtain a mixture comprising p-(benzyloxy)calix[9-20]arenes, p-(benzyloxy)calix[6]arene, p-(benzyloxy)calix[7]arene and p-(benzyloxy)calix[8]arene, in the neutralized form, as defined above, comprising an additional stage of crystallization of the mixture comprising p-(benzyloxy)calix[9-20]arenes, p-(benzyloxy)calix[6]arene, p-(benzyloxy)calix[7]arene and p-(benzyloxy)calix[8]arene in the neutralized form from a mixture of DMSO-based solvents in order to obtain the p-(benzyloxy)calix[6]arene in the neutralized form.

The Inventors have also found that the treatment of the mixture comprising p-(benzyloxy)calix[9-20]arenes, p-(benzyloxy)calix[6]arene, p-(benzyloxy)calix[7]arene and p-(benzyloxy)calix[8]arene in the neutralized form in a mixture of DMSO-based solvents made it possible to isolate p-(benzyloxy)calix[6]arene, p-(benzyloxy)calix[7]arene, p-(benzyloxy)calix[8]arene or a mixture thereof, in the neutralized form, with an excellent yield, greater than or equal to 50%, unlike the prior art.

By the expression "DMSO-based solvent", is meant a solvent mixture comprising at least 10% by volume of DMSO.

The DMSO makes it possible to solubilize the mixture comprising p-(benzyloxy)calix[6]arene, p-(benzyloxy)calix [7]arene and p-(benzyloxy)calix[8]arene in the neutralized form when it is taken up in a solvent.

In an advantageous embodiment, the present invention relates to a process for the preparation of a compound consisting of a mixture comprising p-(benzyloxy)calix[9-20]arenes, p-(benzyloxy)calix[6]arene, p-(benzyloxy)calix[7] arene and p-(benzyloxy)calix[8]arene, as defined above, comprising the following stages:

a. bringing rubidium hydroxide at a total concentration greater than 0.2 equivalent and less than or equal to 0.5 equivalent, in particular 0.3 equivalent, into contact with p-(benzyloxy)phenol and formaldehyde in a solvent, then heating in order to obtain a mixture comprising p-(benzyloxy)calix[9-20]arenes, p-(benzyloxy)calix[6] arene, p-(benzyloxy)calix[7]arene and p-(benzyloxy) calix[8]arene in the salified form, b. neutralization of said mixture comprising p-(benzyloxy) calix[9-20]arenes, p-(benzyloxy)calix[6]arene, p-(benzyloxy)calix[7]arene and p-(benzyloxy)calix[8]arene in the neutralized form, c. optionally, crystallization of the mixture comprising p-(benzyloxy)calix[6]arene and p-(benzyloxy)calix[7] arene in the neutralized form from a mixture of DMSO-based solvents in order to obtain p-(benzyloxy)calix[6] arene, p-(benzyloxy)calix[7]arene, or a mixture thereof, in the neutralized form.

The solvent of stage a. is a solvent with a high boiling point comprised between approximately 100 and approximately 200° C., in particular approximately 140° C., for example xylene, but without being limited thereto.

The heating therefore depends on the nature of the solvent and can be carried out from 30° C. to 200° C.

Stage a. leads to a mixture comprising p-(benzyloxy)calix [9-20]arenes, p-(benzyloxy)calix[6]arene, p-(benzyloxy) calix[7]arene and p-(benzyloxy)calix[8]arene in the salified form.

The neutralization of the mixture is carried out with an acid, for example aqueous hydrochloric acid or aqueous sulphuric acid when the calixarenes are in solution or in suspension in a xylene-type solvent.

In an advantageous embodiment, the present invention relates to a process for the preparation of a compound consisting of a mixture comprising p-(benzyloxy)calix[9-20]arenes, p-(benzyloxy)calix[6]arene, p-(benzyloxy)calix[7]arene and p-(benzyloxy)calix[8]arene, as defined above, comprising the following stages:

a. bringing rubidium hydroxide at a total concentration greater than 0.2 equivalent and less than or equal to 0.5 equivalent, in particular 0.3 equivalent, into contact with p-(benzyloxy)phenol and formaldehyde in a solvent, then heating in order to obtain a mixture comprising p-(benzyloxy)calix[9-20]arenes, p-(benzyloxy)calix[6]arene, p-(benzyloxy)calix[7]arene and p-(benzyloxy)calix[8]arene in the salified form, neutralization of said mixture comprising p-(benzyloxy)calix[9-20]arenes, p-(benzyloxy)calix[6]arene, p-(benzyloxy)calix[7]arene and p-(benzyloxy)calix[8]arene in the neutralized form, b. crystallization of said mixture comprising p-(benzyloxy)calix[9-20]arenes, p-(benzyloxy)calix[6]arene, p-(benzyloxy)calix[7]arene and p-(benzyloxy)calix[8]arene in the neutralized form from a mixture of DMSO-based solvents in order to obtain p-(benzyloxy)calix[6]arene, p-(benzyloxy)calix[7]arene, p-(benzyloxy)calix[8]arene or a mixture thereof, in the neutralized form.

In an advantageous embodiment, the present invention relates to a process for the preparation of a compound consisting of a mixture comprising p-(benzyloxy)calix[9-20]arenes, p-(benzyloxy)calix[6]arene, p-(benzyloxy)calix[7]arene and p-(benzyloxy)calix[8]arene, comprising bringing rubidium hydroxide at a total concentration greater than 0.2 equivalent and less than or equal to 0.5 equivalent, in particular 0.3 equivalent, into contact with p-(benzyloxy)phenol and formaldehyde, as defined above, in which the solvent, in particular xylene, is heated under reflux.

In an advantageous embodiment, the present invention relates to a process for the preparation of a compound consisting of a mixture comprising p-(benzyloxy)calix[9-20]arenes, p-(benzyloxy)calix[6]arene, p-(benzyloxy)calix[7]arene and p-(benzyloxy)calix[8]arene, comprising bringing rubidium hydroxide at a total concentration greater than 0.2 equivalent and less than or equal to 0.3 equivalent, into contact with p-(benzyloxy)phenol and formaldehyde, as defined above, in which the solvent, in particular xylene, is heated under reflux.

In an advantageous embodiment, the present invention relates to a process for the preparation of a compound consisting of a mixture comprising p-(benzyloxy)calix[6]arene and p-(benzyloxy)calix[7]arene, or a compound consisting of p-(benzyloxy)calix[6]arene or p-(benzyloxy)calix[7]arene comprising bringing rubidium hydroxide at a total concentration greater than 0.2 equivalent and less than or equal to 0.5 equivalent, in particular 0.3 equivalent, into contact with p-(benzyloxy)phenol and formaldehyde, as defined above, in which the mixture of solvents of the crystallization stage comprises DMSO and a moderately polar solvent such as acetone.

By "moderately polar solvent", is meant a solvent with a dipole moment close to that of acetone.

The DMSO is mixed with a moderately polar solvent such as acetone in a proportion of 10% to 90% by volume.

The product obtained corresponds to p-(benzyloxy)calix[6]arene, p-(benzyloxy)calix[7]arene, p-(benzyloxy)calix[8]arene or to a mixture thereof.

According to another aspect, the invention relates to a compound consisting of p-(benzyloxy)calix[7]arene in the form of a caesium monosalt.

The compound of the invention can be obtained by synthesis or by salification of p-(benzyloxy)calix[7]arene in the neutralized form by means of at least one base such as caesium hydroxide.

In an advantageous embodiment, the p-(benzyloxy)calix[7]arene, neutral or in the form of a caesium monosalt, has a cavity of approximately 1 nm making it possible in particular to be able to include atoms such as caesium, in particular radioactive caesium.

According to another aspect, the present invention relates to a compound consisting of p-(benzyloxy)calix[7]arene in the form of a caesium monosalt, capable of being obtained by the process comprising a stage of bringing at least one base, in particular caesium hydroxide, into contact with p-(benzyloxy)phenol and paraformaldehyde, in which said base is at a total concentration comprised from 0.09 to 0.2 equivalent, in particular 0.15 equivalent, as defined above.

According to yet another aspect, the present invention relates to the use of a compound consisting of p-(benzyloxy)calix[6]arene, p-(benzyloxy)calix[7]arene, optionally in the form of a caesium salt, or p-(benzyloxy)calix[8]arene, or a mixture thereof, for the constitution of a material.

The calixarenes of the invention can be used in particular for:

the constitution of a composite material for the manufacture of sensitive materials and sensor components or, for the manufacture of a textile material that can be used for the purification of metals, or separation of a pollutant or a contaminant from an aqueous medium or for the separation of uranium or other heavy metals from an aqueous medium.

They can therefore be used:
either alone,
or in a mixture of two:
p-(benzyloxy)calix[7]arene optionally in the form of a caesium salt and p-(benzyloxy)calix[6]arene,
p-(benzyloxy)calix[6]arene and p-(benzyloxy)calix[8]arene,
p-(benzyloxy)calix[7]arene optionally in the form of a caesium salt and p-(benzyloxy)calix[8]arene,
or in a mixture of three:
p-(benzyloxy)calix[7]arene optionally in the form of a caesium salt, p-(benzyloxy)calix[6]arene and p-(benzyloxy)calix[8]arene, In an advantageous embodiment, the calixarenes used above are capable of being obtained by one of the processes defined above.

The invention is illustrated by means of the following examples:

EXAMPLES

Example 1

Obtaining a Compound Consisting of p-(Benzyloxy)Calix[6]Arene or p-(Benzyloxy)Calix[7]Arene in the Form of a Caesium Salt or in Neutralized Form or a Mixture Comprising p-(Benzyloxy)Calix[6]Arene and p-(Benzyloxy)Calix[7]Arene with Caesium Hydroxide

Example 1.1

Concentration of Caesium Hydroxide of 0.15 Equivalent

A suspension of 50.6 g of p-(benzyloxy)phenol (0.254 mol), 20 g (0.667 mol) of paraformaldehyde (melting point:

135° C.) in 700 ml of xylene is placed under argon in a 2-liter three-necked flask equipped with a mechanical stirrer and a "Dean-Stark"-type water recovery system.

The suspension is heated under stirring. When the temperature reaches 90° C., 7.4 ml (0.0425 mol) of a CsOH solution at 50% (by weight) in water is added rapidly using a syringe (and with flushing with argon).

The suspension is left under reflux for 6 hours, during which period the formation of a voluminous white precipitate is observed.

This precipitate is filtered, washed with xylene, then with pentane. m=35 g, yield of p-(benzyloxy)calix[7]arene (in the form of a caesium monosalt): 58% The NMR spectroscopic characteristics of this precipitate correspond to that of the p-(benzyloxy)calix[7]arene monoanion: $^1$H NMR (DMSO-d6): (chemical shifts, ppm) 7.60>delta>7.20 (multiplet, aromatics); 6.72 (singlet end, hydroquinone); 4.93 (singlet end, benzylic protons); 3.71 (singlet end, intracyclic methylenes).

Mass spectrometry (MALDI, DHB matrix): m/z=1617.41 $(M+Cs)^+$.

A 1 g sample of this precipitate is suspended in 5 ml of dichloromethane, then neutralized with a concentrated aqueous solution of HCl, under vigorous stirring for 24 h.

The organic phase is recovered, then evaporated to dryness with a rotary evaporator.

0.91 g of a white solid is recovered, the spectroscopic features of which are perfectly consistent with neutral p-(benzyloxy)calix[7]arene:

$^1$H NMR (DMSO-d6): (chemical shifts, ppm) 7.30 (broad multiplet, aromatics); 6.62 (singlet end, hydroquinone); 4.84 (singlet end, benzylic protons); 3.74 (singlet end, intracyclic methylenes).

Mass spectrometry (MALDI, DHB matrix): m/z=1507.65 $(M+Na)^+$.

The loss of weight observed (90 mg) is completely consistent with that expected for the neutralization of a caesium monosalt: (p-(benzyloxy)calix[7]arene-)$^-$. $Cs^+$)→p-(benzyloxy)calix[7]arene.

Example 1.2

Concentration of Caesium Hydroxide of 0.3 Equivalent

A suspension of 50.6 g of p-(benzyloxy)phenol (0.254 mol), 20 g (0.667 mol) of paraformaldehyde (melting point: 135° C.) in 700 ml of xylene is placed under argon in a 2-L three-necked flask equipped with a mechanical stirrer and a "Dean-Stark"-type water recovery system.

The suspension is heated under stirring. When the temperature reaches 90° C., 14.8 ml (0.085 mol) of a solution of CsOH at 50% (by weight) in water is added rapidly using a syringe (and with flushing with argon).

The suspension is left under reflux for 5 hours 30 minutes. A perfectly clear bright orange solution is then obtained.

100 ml of an HCl solution at 37% in water is then added, and the formation of a precipitate is observed. The suspension is left under vigorous stirring over a WE, then evaporated to dryness in a rotary evaporator.

After washing with 500 ml of water (removal of the salts and the excess HCl), the solid is dissolved while hot (130° C.) in 200 ml of DMSO. A clear black solution is then obtained, to which 2 l of acetone is added while hot.

After returning to ambient temperature, this clear solution is left for a week, during which period a crystalline precipitate of p-(benzyloxy)calix[6]arene (18 g) is deposited on the walls of the flask.

The filtrate originating from this last recovery is evaporated in a rotary evaporator, then with a heat gun until a black solid is obtained. This solid is washed with acetone, which leads to the recovery of a second batch of p-(benzyloxy)calix[6]arene (10 grams).

Total mass of p-(benzyloxy)calix[6]arene: 28 g, yield 51%.

$^1$H NMR (DMSO-d6): (chemical shifts, ppm) 7.30 (broad multiplet, aromatics); 6.62 (singlet end, hydroquinone); 4.79 (singlet end, benzylic protons); 3.72 (singlet end, intracyclic methylenes).

Mass spectrometry (MALDI, DHB matrix): m/z=1295.49 $(M+Na)^+$

Example 2

Obtaining a Compound Consisting of p-(Benzyloxy) Calix[6]Arene or p-(Benzyloxy)Calix[7]Arene in the Neutralized Form or p-(Benzyloxy)Calix[8]Arene or a Mixture Comprising p-(Benzyloxy)Calix[6]Arene, p-(Benzyloxy)Calix[7]Arene and p-(Benzyloxy) Calix[8]Arene with Sodium or Potassium Hydroxide Example 2.1

Concentration of Sodium or Potassium Hydroxide of 0.15 Equivalent

A suspension of 34.5 g of p-(benzyloxy)phenol (0.173 mol), 20 g (0.667 mol) of paraformaldehyde (melting point: 135° C.) in 450 ml of xylene is placed under argon in a 1 L three-necked flask equipped with a mechanical stirrer and a "Dean-Stark"-type water recovery system.

The suspension is heated under stirring. When the temperature reaches 95° C., a solution of 1.43 g (0.03 mol) of KOH in 6 ml of Millipore water is added rapidly using a syringe (and with flushing with argon). The immediate appearance of yellow colouring is observed.

The reaction medium is taken to reflux for 3 hours 30 minutes, during which period the formation of an abundant white precipitate and a bright orange solution is observed.

After returning to ambient temperature, the precipitate is recovered by filtration, washed with 100 ml of xylene and 300 ml of pentane.

Analysis of this precipitate indicates that it is constituted by pure p-(benzyloxy)calix[7]arene. M=20 g, yield 54%.

Characterizations:

$^1$H NMR (DMSO-d6): (chemical shifts, ppm) 7.30 (broad multiplet, aromatics); 6.62 (singlet end, hydroquinone); 4.84 (singlet end, benzylic protons); 3.74 (singlet end, intracyclic methylenes).

Mass spectrometry (MALDI, DHB matrix): m/z=1524.62 $(M+K)^+$.

Example 2.2

Concentration of Sodium or Potassium Hydroxide of 0.3 Equivalent

A suspension of 51.5 g of p-(benzyloxy)phenol (0.258 mol), 20 g (0.667 mol) of paraformaldehyde (melting point: 135° C.) in 700 ml of xylene is placed under argon in a 2-L three-necked flask equipped with a mechanical stirrer and a "Dean-Stark"-type water recovery system.

The suspension is heated under stirring. When the temperature reaches 90° C., 3.056 g of NaOH (0.0764 mol) in 10 ml of water is added rapidly using a syringe (and with flushing with argon).

The suspension is left under reflux for 4 hours 30 minutes, at the end of which period the reaction medium solidifies.

After returning to ambient temperature, the reaction medium is neutralized with 500 ml of a 2M solution of HCl, under very vigorous stirring.

The resulting emulsion is evaporated to dryness and washed with 500 ml of water (removal of the sodium salts).

The resulting orange-coloured solid is washed with 500 ml of THF and the resulting white precipitate is filtered out, which leads to the recovery of 20 g of pure p-(benzyloxy) calix[8]arene.

Yield: 36.6%.

$^1$H NMR (DMSO-d6): (chemical shifts, ppm) 7.30 (broad multiplet, aromatics); 6.58 (singlet end, hydroquinone); 4.80 (singlet end, benzylic protons); 3.77 (singlet end, intracyclic methylenes).

Mass spectrometry (MALDI, DHB matrix): m/z=1719.62 (M+Na)$^+$.

The corresponding filtrate is evaporated to dryness, and dissolved while hot in 45 ml of DMSO, which leads to the formation of a homogeneous black solution. 1 L of toluene is added, and the clear dark orange solution is placed in a freezer (−23° C.) for 1 week, which leads to the formation of a microcrystalline precipitate. This precipitate is filtered, and its analysis by $^1$H NMR shows that it is pure p-(benzyloxy) calix[6]arene. M=6.3 g, 11%.

$^1$H NMR (DMSO-d6): (chemical shifts, ppm) 7.30 (broad multiplet, aromatics); 6.62 (singlet end, hydroquinone); 4.79 (singlet end, benzylic protons); 3.72 (singlet end, intracyclic methylenes).

Mass spectrometry (MALDI, DHB matrix): m/z=1295.49 (M+Na)$^+$.

The corresponding DMSO/toluene filtrate is evaporated off until an orange-coloured liquid is obtained. After 1 l of methanol is added, followed by filtration, 28.5 g of pure p-(benzyloxy)calix[7]arene is recovered. Yield: 52%.

$^1$H NMR (DMSO-d6): (chemical shifts, ppm) 7.30 (broad multiplet, aromatics); 6.62 (singlet end, hydroquinone); 4.84 (singlet end, benzylic protons); 3.74 (singlet end, intracyclic methylenes).

Mass spectrometry (MALDI, DHB matrix): m/z=1524.62 (M+K)$^+$.

Example 3

Obtaining a Compound Consisting of a Mixture Comprising p-(Benzyloxy)Calix[6]Arene, p-(Benzyloxy)Calix[7]Arene, p-(Benzyloxy)Calix[8]Arene and a Mixture of p-(Benzyloxy)Calix[9-20]Arenes with Rubidium Hydroxide In a 2-1 flask equipped with a magnetic stirrer and a Dean-Stark apparatus, a suspension of 50 g of 4-(benzyloxy)phenol (0.25 equivalents), 15 g of paraformaldehyde (0.5 equivalents) in 670 ml of xylene (mixture of isomers) is prepared.

This suspension is heated. At 90° C., 9 ml (0.3 equivalent with respect to the phenol) of a solution of RbOH at 50% by weight in water is added rapidly.

The solution is taken to reflux for 6 hours, then returned to ambient temperature.

The suspension is neutralized with 500 ml of THF containing 30 ml of a solution of HCl at 37% under vigorous stirring.

The resulting fluid suspension is filtered, and the filtrate evaporated to dryness. The solid obtained is washed with 500 ml of acetonitrile and filtered (to remove the most polar species, such as the linear oligomer radicals, calix[5]arene and homooxacalixarene).

After filtration and drying with a vacuum pump, 32 g of a brown solid is recovered, which is dissolved while hot in a mixture of 75 ml of DMSO and 750 ml of acetone, and immediately filtered (recovery of p-(benzyloxy)calix[8] arene).

The resulting dark orange clear solution is left in the refrigerator for two days, during which period a microcrystalline precipitate (20 g) is formed.

An NMR study shows that this precipitate is constituted exclusively by large calixarenes.

$^1$H NMR (DMSO-d6): (chemical shifts, ppm) 7.30 (broad multiplet, aromatics); 6.52 (singlet end, hydroquinone); 4.77 (singlet end, benzylic protons); 3.84 (broad singlet, intracyclic methylenes).

Mass spectrometry MALDI (DHB matrix):
2568.97, p-(benzyloxy)calix[12]arene.Na; 2782.07 p-(benzyloxy)calix[13]arene.Na; 2994.14, p-(benzyloxy) calix[14]arene.Na; 3206.24, p-(benzyloxy)calix[15]arene.Na; 3418.31, p-(benzyloxy)calix[16]arene.Na.

The filtrate from recovery of the previous precipitate is evaporated firstly in a rotary evaporator (removal of acetone), then with a vacuum pump (removal of DMSO) at 60° C. When the DMSO concentrate begins to solidify, pumping is stopped, and the highly viscous solid obtained is washed with 100 ml of acetone, and filtered.

15 g of p-(benzyloxy)calix[6]arene is obtained. Yield: 30%.

The invention claimed is:

1. A process for the preparation of a compound selected from the group consisting of a mixture comprising p-(benzyloxy)calix[6]arene, p-(benzyloxy)calix[7]arene and p-(benzyloxy)calix[8]arene; a mixture comprising p-(benzyloxy) calix[6]arene and p-(benzyloxy)calix[7]arene; a mixture comprising p-(benzyloxy)calix[7]arene and p-(benzyloxy) calix[8]arene; a mixture comprising p-(benzyloxy)calix[6] arene and p-(benzyloxy)calix[8]arene; p-(benzyloxy)calix [6]arene; p-(benzyloxy)calix[7]arene; and p-(benzyloxy) calix[8]arene, said process comprising:
a stage of bringing caesium hydroxide into contact with p-(benzyloxy)phenol and paraformaldehyde, said caesium hydroxide being at a total concentration of 0.09 equivalent to 0.5 equivalent with respect to said p-(benzyloxy)phenol.

2. The process according to claim 1, wherein said caesium hydroxide is at a total concentration comprised from 0.09 to 0.2 equivalent in order to obtain a mixture comprising p-(benzyloxy)calix[6]arene and p-(benzyloxy)calix[7]arene in the salified form.

3. The process according to claim 2, further comprising: a stage of filtration of the mixture comprising p-(benzyloxy) calix[6]arene and p-(benzyloxy)calix[7]arene in the salified form, in order to obtain p-(benzyloxy)calix[7]arene in the form of a caesium monosalt followed by a stage of neutralization of p-(benzyloxy)calix[7]arene in the form of a caesium monosalt in order to obtain p-(benzyloxy)calix[7]arene in the neutralized form.

4. The process according to claim 2, comprising the following stages:
a) bringing caesium hydroxide at a concentration from 0.09 to 0.2 equivalent into contact with p-(benzyloxy)phenol and paraformaldehyde in a solvent, then heating in order to obtain a mixture comprising p-(benzyloxy)calix[6] arene and p-(benzyloxy)calix[7]arene in the salified form, and
b) neutralization of the mixture comprising p-(benzyloxy) calix[6]arene and p-(benzyloxy)calix[7]arene in the salified form with an acid, in order to obtain a mixture comprising p-(benzyloxy)calix[6]arene and p-(benzyloxy)calix[7]arene in the neutralized form.

5. The process according to claim 1, wherein said caesium hydroxide is at a total concentration greater than 0.2 equivalent and less than or equal to 0.5 equivalent in order to obtain a mixture comprising p-(benzyloxy)calix[6]arene and p-(benzyloxy)calix[7]arene in the salified form.

6. The process according to claim 5, further comprising a stage of neutralization of the mixture comprising p-(benzyloxy)calix[6]arene and p-(benzyloxy)calix[7]arene obtained in the salified form in order to obtain a mixture comprising p-(benzyloxy)calix[6]arene and p-(benzyloxy)calix[7]arene in the neutralized form.

7. The process according to claim 6, further comprising a stage of crystallization of the mixture comprising p-(benzyloxy)calix[6]arene and p-(benzyloxy)calix[7]arene in the neutralized form from a mixture of DMSO- or DMF-based solvents in order to obtain p-(benzyloxy)calix[6]arene in the neutralized form.

8. The process according to claim 5, comprising the following stages:
   a) bringing caesium hydroxide at a total concentration greater than 0.2 equivalent and less than or equal to 0.5 equivalent into contact with p-(benzyloxy)phenol and formaldehyde in a solvent, then heating in order to obtain a mixture comprising p-(benzyloxy)calix[6]arene and p-(benzyloxy)calix[7]arene in the salified form,
   b) neutralization of said mixture comprising p-(benzyloxy)calix[6]arene and p-(benzyloxy)calix[7]arene in the salified form with an acid in order to obtain a mixture comprising p-(benzyloxy)calix[6]arene and p-(benzyloxy)calix[7]arene in the neutralized form,
   c) optionally, crystallizing the mixture comprising p-(benzyloxy)calix[6]arene and p-(benzyloxy)calix[7]arene in the neutralized form from a mixture of DMSO- or DMF-based solvents in order to obtain p-(benzyloxy)calix[6]arene in the neutralized form.

9. A compound consisting of p-(benzyloxy)calix[7]arene in the form of a caesium monosalt.

10. A compound consisting of p-(benzyloxy)calix[7]arene in the form of a caesium monosalt capable of being obtained by the process as defined in claim 3.

11. The process according to claim 2, in which said caesium hydroxide is at a total concentration comprised 0.15 equivalent in order to obtain a mixture comprising p-(benzyloxy)calix[6]arene and p-(benzyloxy)calix[7]arene in the salified form.

12. The process according to claim 4, comprising the following stages:
   a) bringing caesium hydroxide at a concentration of 0.15 equivalent into contact with p-(benzyloxy)phenol and paraformaldehyde in a solvent, then heating in order to obtain a mixture comprising p-(benzyloxy)calix[6]arene and p-(benzyloxy)calix[7]arene in the salified form, and
   b) neutralizing the mixture comprising p-(benzyloxy)calix[6]arene and p-(benzyloxy)calix[7]arene in the salified form with an acid, in order to obtain a mixture comprising p-(benzyloxy)calix[6]arene and p-(benzyloxy)calix[7]arene in the neutralized form.

13. The process according to claim 5, wherein said caesium hydroxide is at a total concentration of 0.3 equivalent in order to obtain a mixture comprising p-(benzyloxy)calix[6]arene and p-(benzyloxy)calix[7]arene in the salified form.

14. The process according to claim 8, comprising the following stages:
   a) bringing caesium hydroxide at a total concentration of 0.3 equivalent into contact with p-(benzyloxy)phenol and formaldehyde in a solvent, then heating in order to obtain a mixture comprising p-(benzyloxy)calix[6]arene and p-(benzyloxy)calix[7]arene in the salified form,
   b) neutralizing said mixture comprising p-(benzyloxy)calix[6]arene and p-(benzyloxy)calix[7]arene in the salified form with an acid in order to obtain a mixture comprising p-(benzyloxy)calix[6]arene and p-(benzyloxy)calix[7]arene in the neutralized form, and
   c) optionally, crystallizing the mixture comprising p-(benzyloxy)calix[6]arene and p-(benzyloxy)calix[7]arene in the neutralized form from a mixture of DMSO- or DMF-based solvents in order to obtain p-(benzyloxy)calix[6]arene in the neutralized form.

* * * * *